(12) United States Patent
Gordon

(10) Patent No.: US 6,771,190 B2
(45) Date of Patent: Aug. 3, 2004

(54) SIGNALLING APPARATUS FOR THE PHYSICALLY DISABLED

(76) Inventor: Gary Gordon, 21112 Bank Mill Rd., Saratoga, CA (US) 95070

(*) Notice: Subject to any disclaimer, the term of this patent is extended or adjusted under 35 U.S.C. 154(b) by 0 days.

(21) Appl. No.: 10/299,462

(22) Filed: Nov. 19, 2002

(65) Prior Publication Data
US 2004/0095245 A1 May 20, 2004

(51) Int. Cl.⁷ .............................................. G08G 1/123
(52) U.S. Cl. ............... 340/999; 340/573.1; 340/825.19; 340/666; 5/654
(58) Field of Search .............................. 340/999, 573.1, 340/825.19, 591, 665, 666, 667, 575; 137/884; 434/112; 307/118, 144; 303/1; 5/713, 915, 654

(56) References Cited

U.S. PATENT DOCUMENTS

| | | | | |
|---|---|---|---|---|
| 3,691,569 A | * | 9/1972 | Ikada | 5/655.9 |
| 4,681,992 A | * | 7/1987 | Kazmierski | 200/82 E |
| 4,982,466 A | * | 1/1991 | Higgins et al. | 5/713 |
| 5,121,513 A | * | 6/1992 | Thomas et al. | 5/713 |

* cited by examiner

Primary Examiner—Anh V. La

(57) ABSTRACT

A signaling device for disabled persons uses a pneumatic system comprised of a special cushion, an air bleed to ambient, and a sensitive air-pressure sensor. The cushion may also serve as a head, limb, or body support. The cushion is foam-filled and self-inflating, and is capable of supporting static loads without the need for its being pressurized. A user initiates the generation of a signal by bumping the cushion, as for example with a backwards jerk of their head or a sideways kick of a limb. The resulting momentary surge in system pressure is sensed by the air-pressure switch, which is set to trip at 1/1000 of an atmosphere. The momentary closing of the contacts of the pressure switch are used to signal other assistive appliances, such as computer software for generating text. Because of the air bleed, the momentary pressure surge causes some air to rush out, which is immediately replenished due to suction from the foam-filled cushion, returning the system gauge pressure towards zero, Since static loads are supported by the foam cushion and not by air pressure, they do not cause continuous signals. Because the apparatus eliminates the alignment need between a switch and a separate body support, it adjusts to a user's changing posture, enabling them to signal rapidly and accurately after extended use.

10 Claims, 2 Drawing Sheets

SIGNALLING APPARATUS FOR THE PHYSICALLY DISABLED

BACKGROUND

1. Field of the Invention

This invention relates to assistive aids for the physically challenged. More specifically, it relates to aids for sensing gross body motions such as nods of the head or motions of a limb, for the purpose of signaling other assistive appliances such as computer speech software.

2. Description of Prior Art

Several medical disorders including cerebral palsy cause loss of muscle control, and in severe cases speech loss, making it difficult or nearly impossible for some people to communicate. One useful aid is E Z Keys from Words+Inc., which allow one to form words and sentences by making selections from menus. Such selections may be made by the user closing a switch, as for example by a movement of their head. For example, such a switch might be placed above and behind a head rest, where it can be reached by a user if they arch their head upwards and backwards. Such switches are available from AbleNet Inc. Another switch, the "Petite Pillow Switch from Toys for Special Children Inc. uses a balloon-bladder to sense when a person reaches out and presses on it. Other similar concepts are disclosed in the "Educational Organizer" of U.S. Pat. No. 5,601,432.

Unfortunately, none of these switches can support static loads, such as a person's head or limb, because they would always be switched on. Often, for them to work at all, they must be used together with a supplemental support such as a head rest. The problem then becomes aligning the switch to the support, which is seldom long-lasting, because individuals who require such devices will likely not have sufficient muscle control to maintain a particular posture. The problem is compounded by the user likely not being able to communicate which adjustments are best, with the result usually being a poor compromise. Further, the alignment is often so complicated as to be beyond the skills of alternative care-givers, and merely changing a seating angle can ruin an otherwise good alignment. For many users, these switches are a constant source of frustration and aggravation.

What is needed is a comfortable assistive switch that is easy to set up, and is self-accommodating of a user's changing posture.

SUMMARY OF THE INVENTION

The present invention is an improved and self-adjusting sensing and signaling device for the disabled. The device senses human contact bumps, and beneficially is not affected by static loads or shifting postures.

The apparatus may be characterized as a being a pneumatic system. It's first key component is a small cushion, which importantly is self-inflating. This is accomplished preferably by its being filled with an elastomeric foam. When a user desires to send a signal, and bumps or otherwise presses anywhere on the cushion, the air pressure in the cushion momentarily increases slightly, typically less than one percent.

This brief pressure increase is detected by a second key component, a sensitive air pressure sensor. This sensor in its simplest form is a pressure switch, whose electrical contacts can be used to signal a computer or other electronic device.

An important third component of the pneumatic apparatus is an air bleed, which slowly over many seconds equalizes the pressure inside and outside the system. The function of the bleed is to allow the apparatus to be self-adjusting. By equalizing the gauge pressure inside and outside the system, the switch will not close under the weight of static loads such as body weight. Instead, the weight of the load is supported by the comfortable elastomeric form inside the cushion. Thus the apparatus is able to also act as a body support, without generating continuous signals.

By providing service as both a body support and a signaling device, the apparatus overcomes the limitation of previous devices, that of requiring complicated and impermanent alignments. In the present apparatus, such alignment is automatic and long-lasting, and also accommodating of shifts in a user's body posture. Its soft cushion is more comfortable than a hard switch. Users become able to send signals many times more rapidly and many times more controllably, even after hours and hours of extended use.

DESCRIPTION OF A PREFERRED EMBODIMENT

Figure 1:
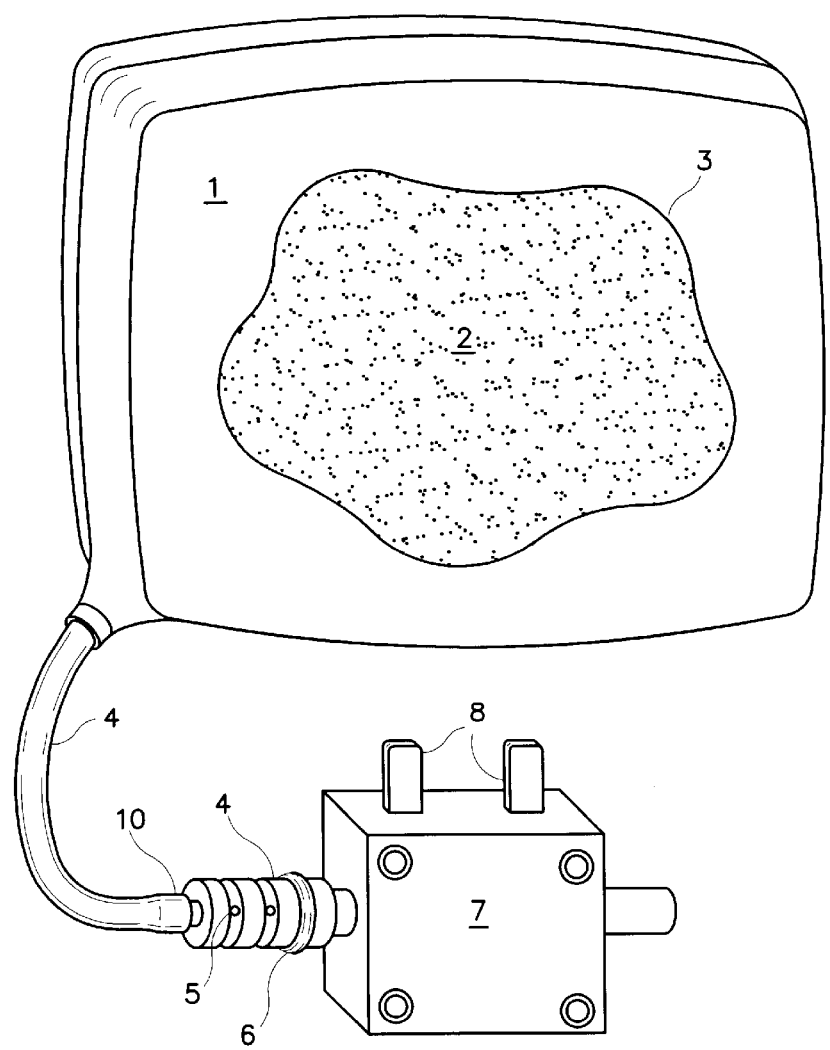
FIG. 1 depicts the key components of the preferred embodiment.

Referring to FIG. 1, shown therein are the three key components of the present invention. The first component is a self-inflating cushion 1. This cushion may be any suitable size, however for a head switch an appropriate size would be 1.5"×4"×6". This cushion is filled with a porous elastomeric foam 2, as is seen through cutaway 3. The purpose of the foam is to give internal support to cushion support, causing it to self-inflate, without the need for applying forced air, as would be the case for a balloon or balloon tire. The strength of the foam should be sufficient to support a weight of one's head or limb, i.e., of the order of ten pounds. Such a cushion may be readily constructed using technologies similar to those used in the camping and medical products manufactured by the Thermarest Corporation.

A flexible tube 4 pneumatically couples the cushion 1 to the air bleed manifold 4. This tube may be a length of Tygon tubing. If the cushion is an adapted Thermarest product, then this tube would replace the normal inflation valve.

The air bleed manifold 4, which provides the controlled air leak through holes 5, may be a turned part made out of thick-wall seamless stainless steel tubing. In it are cut three circular grooves. At the bottom of each groove is drilled an air bleed hole 5, through the wall of the manifold. The air bleed holes are of size 0.020", 0.029", and 0.038", each providing approximately three times the airflow as the previous. To control the amount of air bleed, the holes 5 may be selectively blocked by snapping O-rings 6 into their associated grooves.

In this preferred embodiment, this sensor is simply a pressure switch. The switch contacts should close at a pressure of several tenths of an inch of water, or approximately one thousandth of an atmosphere. A suitable switch is a the PSF200A pressure switch manufactured by World Magnetics Inc. The terminals 8 of the switch may be connected to electrical signaling circuits.

The operation of the preferred embodiment will be described in terms of its use as a combined head rest and sensor, for sensing being bumped by intentional backwards jerks or bounces of one's head. Also to be described is how the system equilibrates, as a user is first seated in a semi-reclining position, with the back of their head coming to rest on the cushion.

Figure 3A:
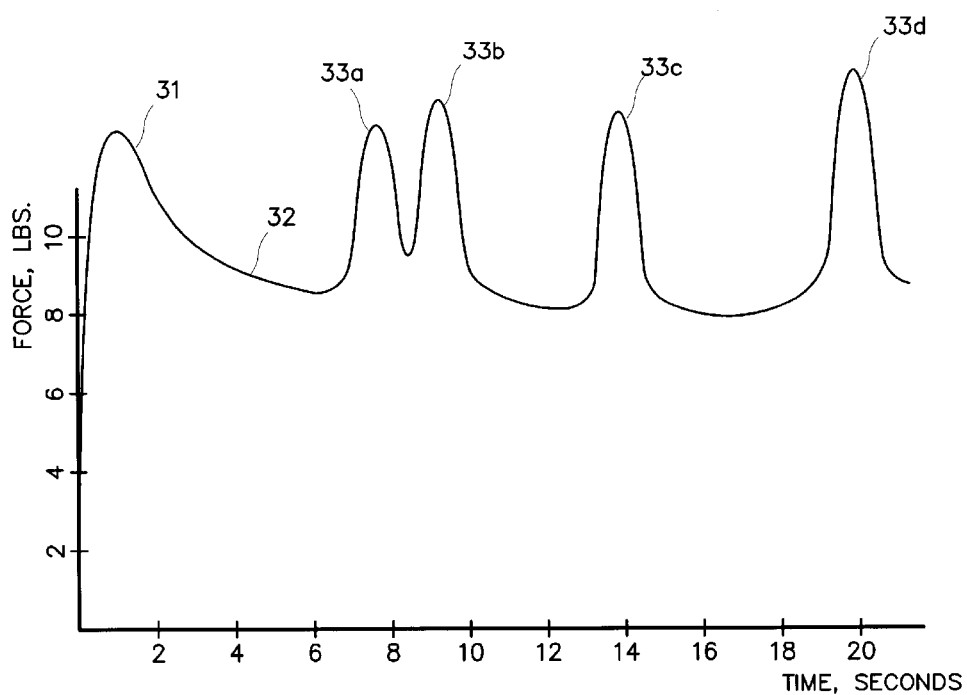
FIG. 3 shows the operation of the present invention, in terms of the forces applied, the system pressures produced, and the signals generated.
Figure 3B:
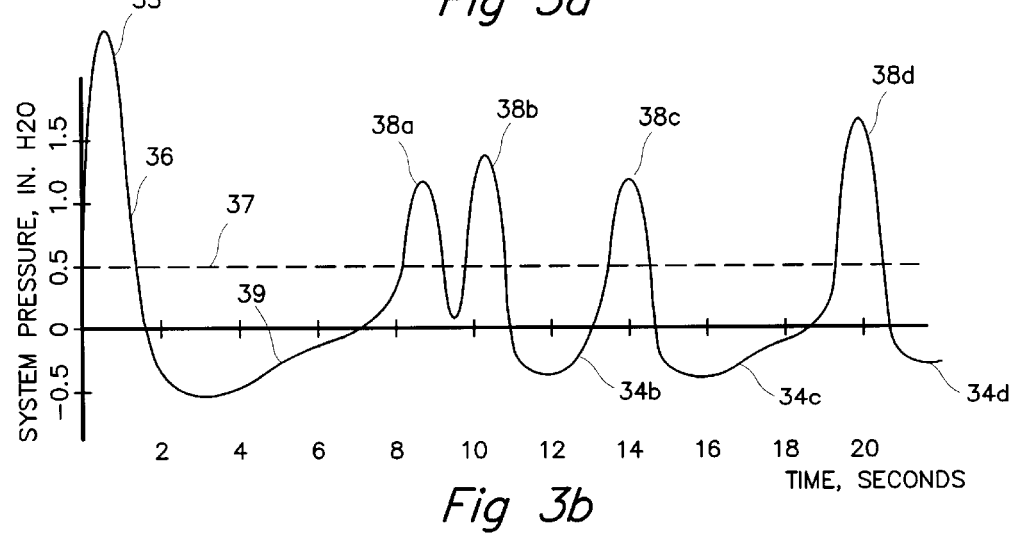
Figure 3C:
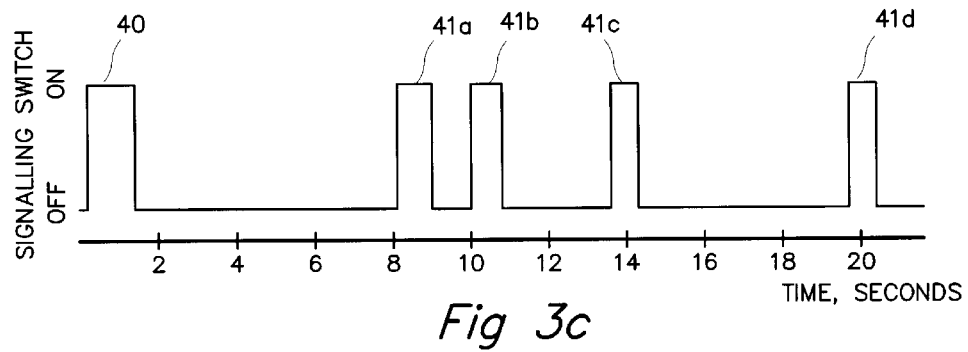

Referring now to FIGS. 3a, 3b, and 3c, there are shown three waveforms. The first waveform in FIG. 3a shows the force generated by the weight of the user's head, first as it first comes to rest on the cushion, and subsequently as is arched backwards with the intent of generating signals. This force 31 will likely first overshoot, due to momentum, and then settle out to a quiescent value 32. Once settled, whenever the user actuates the system by bumping the cushion with their head, they will produce short force pulses 33a, 33b, 33c, 33d superimposed upon the quiescent force 32.

Referring now to FIG. 3b there is shown the pressure inside the pneumatic system. Also shown is a dotted line 37 at a suggested pressure switch setting of 0.5 inches-of-water, although settings between 0.1 inches and 0.5 inches all work very well. Were it not for the air bleed 4 provided in the present system, the pressure curve 35, 36, 39, 38a, 38b, 38c, 38d would mimic the force curve of FIG. 3a. Further, due to the weight of the user's head, the pressure curve would lie continually above the switch threshold, and undesirably hold the switch on continuously. To prevent this, the air bleed 4 causes the quiescent pressure 39 in the system to always seek the ambient air pressure, which is the equivalent to saying that it always seeks zero gauge pressure. This zero gauge pressure is represented by the X-axis of this FIG. 3b. Since the average gauge pressure in the system will always be zero, the instantaneous gauge pressures will frequently be negative 34a, 34b, 34c, 34d, corresponding to absolute pressures less than atmospheric pressure. During these intervals of negative pressure, the system is refilling the air lost through the bleed during bumps. The refilling is produced by the action of the self-inflating cushion sucking air back into the system. Indeed, in normal operation, the gauge pressure often tends to alternate between being positive and negative 38b, 34b, 38c, 34c, 38d, 34d.

It is seen that even though the user's head is continually applying a static force, the system pressure only swings significantly positive when the cushion is intentionally bumped, causing the switch threshold 37 to be traversed 38a, 38b, 38c, 38d. The system is responsive to velocities and brief applications of force, but not to static forces.

Referring now to FIG. 3c, there is shown the response of the pressure switch 7 to the pressure pulses of FIG. 3b. Whenever the pressure exceeds the pressure threshold 37, the switch actuates, or closes, changing to its ON state 40, 41a, 41b, 41c, 41d. When pressure drops below the same threshold 37, the switch de-actuates, or opens, changing to its off state. Note that a transient false switch signal 40 is generated once, while the system adjusts to the static load. Thereafter, signaling pulses 41a, 41b, 41c, 41d are only in response to intentional head-bumps applied to the cushion.

The time the system takes to equilibrate is characterized by its time-constant, which is set by the air bleed, and by the collective volume of the pneumatic system. The smaller the pneumatic volume and the larger the bleed orifice, the shorter the time constant. Desirably, this time constant is set between 0.1 and 1000 seconds, and more desirably, between 1 and 10 seconds.

Figure 2:
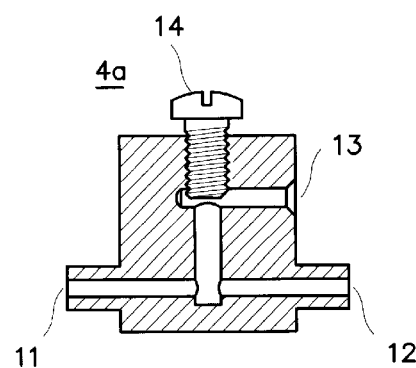
FIG. 2 shows an adjustable alternative air bleed.

Setting the time constant is an important consideration in customizing the system for an individual user. If it is set too long, then normal body motions such as posture changes may undesirably generate signals. On the other hand, if it is set too short, a user with less vitality may be unable to generate signals at all. The optimum setting will vary, so means may be provided for adjusting the time constant by varying the amount of air bleed. FIG. 2 shows such an adjustable alternative air bleed 4a. An adjustment screw 14 controls the degree that air passing through the channel 11, 12 will escape via an orifice 13.

The pneumatic system should free from extraneous leaks. Any such leak will act as a supplemental air bleed, and change the time constant of the system. The pneumatic system may be tested for such leaks by first shutting off the air bleed. Then a weight can be placed atop the cushion, sufficient to actuate the pressure sensor or switch. If, the switch stays closed for hours, then the pneumatic system is free from leaks. Such a system with the air bleed shut off characterizes in part the pneumatic signaling switches of the old art, which require not having any air bleeds.

Performing this test instead on a properly operating embodiment of the present invention, with the air bleed once-again re-enabled, will cause the switch to only stay closed for a while, less than an hour, and usually less than minutes or seconds. Indeed, if the switch eventually opens, it is indicative that the pneumatic system at hand is not old art, but rather the art the present invention.

While what has been described has been the preferred embodiments, nonetheless many variations are within the scope of the claims. For example, while for convenience and clarity the invention has been described in terms of a head rest switch, the invention is intended more broadly as a sensing support for any part of the body that still has motor function, including the torso, arms, legs, hands, fingers, or feet.

There are also many mechanical variations possible for each component of the apparatus. For example, the air bleed 4, 4a could simply be a small conventional adjustable valve. Similarly, there are many ways to uncover the holes 5 of FIG. 1, such as sliding piece of tubing, or removable set screws. Further, although not necessarily to be recommended, the function of the air bleed could be accomplished by integrating it into other parts of the system, such as intentionally fitting the system with leaky connections 10, or a leaky cushion or pressure switch. Also not necessarily to be recommended, the air bleed could be a more complicated arrangement of check valves, in which the outflow and inflow used separate passages.

Instead of the pressure switch 7, a pressure transducer (not shown) may be employed, such as those available from National Semiconductor. Such transducers may have an impedance that changes, while others provide a voltage or current output that is proportional to air pressure. This voltage or current may be sensed by a threshold detector, an analog-to-digital converter, or left up to the computer interface or other device to determine when a bump or other event has caused an increase in pressure. When such a determination has been made that the pressure is above a predetermined threshold, any such sensor may be considered to be activated or actuated, and when it drops below the same or a different threshold, it may be considered deactivated or de-actuated. Any of the pressure sensors may optionally have the property of hysteresis.

For the purposes of the present invention, "generates a signal" is meant broadly, and includes generating any electrical signal. The term also is meant to include modulating the flow of energy in an external circuit. For example, the pressure sensor could be a pressure switch in series with an external circuit, and closing or opening the switch would constitute generating a signal. In another example, the pressure sensor could be a variable resistor, capacitor, or inductor, whose value changes with pressure, and would constitute generating a signal.

Lastly, multiple cushions 1 may be connected together in parallel. Further, any cushion may variously be thought of as a pad or a pillow, and may be rendered self-inflating by means other than by being foam-filled 2. For example, it may be fitted with internal springs or other supports, or have an exterior surface made of a material that has memory and naturally springs back to its original shape.

I claim:

1. An apparatus for facilitating signaling by the physically disabled, said apparatus comprising:

a pneumatic system;

said system including a self-inflating cushion;

said system further including an air bleed to ambient air pressure outside the system;

and said system further including an air pressure sensor;

wherein said cushion self-inflates without the application of electrical or air or other form of applied power, and wherein the air pressures inside and outside the system are equalized by airflow through the air bleed, and wherein when the cushion is bumped, it causes a momentary increase in air pressure inside the system, and wherein said increase is sensed by the pressure sensor, which generates a signal for use by external devices.

2. The apparatus as recited in claim 1 wherein the cushion self-inflates as a consequence of being filled with an elastomeric foam.

3. The apparatus as recited in claim 1 wherein the pressure sensor is a pressure switch.

4. The apparatus as recited in claim 3 wherein the signal is a contact closure.

5. The apparatus as recited in claim 1 wherein the air-bleed includes an orifice that is adjustable.

6. The apparatus as recited in claim 1 wherein the air-bleed orifice is a plurality of orifices which may be individually opened or closed.

7. The apparatus as recited in claim 1 wherein the air-bleed orifice consists of incidental leakage as a consequence of the pneumatic system not being tightly sealed.

8. The apparatus as recited in claim 1 wherein, upon placing a weight atop the cushion, the gauge pressure in the system initially increases, and whereupon after an elapsed time of ten minutes have passed, the pressure has dropped more than 50% of the way back to ambient pressure.

9. The apparatus as recited in claim 1 wherein further upon placing a weight atop the cushion, the pressure sensor actuates, and whereupon after an elapsed time of ten minutes have passed, the pressure sensor has already de-actuated.

10. The apparatus as recited in claim 1 wherein the gauge pressure of the pneumatic system alternates between being positive and being negative.

* * * * *